(12) United States Patent
Wang

(10) Patent No.: US 9,019,497 B2
(45) Date of Patent: Apr. 28, 2015

(54) MEASUREMENT OF LINEAR AND CIRCULAR DIATTENUATION IN OPTICAL ELEMENTS

(75) Inventor: Baoliang Wang, Beaverton, OR (US)

(73) Assignee: Hinds Instruments Inc., Hillsboro, OR (US)

( * ) Notice: Subject to any disclaimer, the term of this patent is extended or adjusted under 35 U.S.C. 154(b) by 1625 days.

(21) Appl. No.: 12/298,762

(22) PCT Filed: May 1, 2007

(86) PCT No.: PCT/US2007/067949
§ 371 (c)(1),
(2), (4) Date: Mar. 25, 2009

(87) PCT Pub. No.: WO2007/130990
PCT Pub. Date: Nov. 15, 2007

(65) Prior Publication Data
US 2009/0323064 A1    Dec. 31, 2009

Related U.S. Application Data

(60) Provisional application No. 60/746,167, filed on May 1, 2006.

(51) Int. Cl.
*G01J 4/00* (2006.01)
*G01N 21/19* (2006.01)
*G01M 11/02* (2006.01)

(52) U.S. Cl.
CPC ........... *G01N 21/19* (2013.01); *G01M 11/0285* (2013.01)

(58) Field of Classification Search
USPC .................................. 356/365–370, 432–444
See application file for complete search history.

(56) References Cited

U.S. PATENT DOCUMENTS

| 5,504,581 | A | 4/1996 | Nagata | |
|---|---|---|---|---|
| 5,636,023 | A * | 6/1997 | Yanagisawa | 356/613 |
| 6,765,671 | B2 * | 7/2004 | Priestley | 356/365 |
| 2003/0227622 | A1 | 12/2003 | Priestley | |
| 2004/0075834 | A1 | 4/2004 | Kaplan | |
| 2005/0219528 | A1 * | 10/2005 | Wang | 356/365 |
| 2006/0062351 | A1 * | 3/2006 | Yokhin et al. | 378/86 |

OTHER PUBLICATIONS

Chenault, "Measurements of linear diattenuation and linear retardance spectra with a rotating sample spectropolarimeter." Applied Optics USA V 32, No. 19, Jul. 1993; pp. 3513-3519.

(Continued)

*Primary Examiner* — Tarifur Chowdhury
(74) *Attorney, Agent, or Firm* — Hancock Hughey LLP

(57) ABSTRACT

A system for measuring linear or circular diattenuation in an optical element includes a sample rotation stage for securing an optical element sample; a light source module for generating a source light beam and a detector module. The light source module and detector module are arranged with the sample rotation stage between them, thereby permitting the source light beam to propagate through a sample that may be secured in the sample stage and to the detector module. Linear motion control of the light source module and the detector module, as well as tilt control of the light source module, the sample rotation stage and the detector module is provided, thereby to facilitate detection, by the detector module of the modulated light intensity information corresponding to a diattenuation characteristic of the optical sample secured in the sample stage.

16 Claims, 6 Drawing Sheets

(56) References Cited

OTHER PUBLICATIONS

McQuire, "Polarization aberrations. 1. Rotationally symmetric optical systems" Applied Optics USA, v 33 No. 22 Aug. 1994, pp. 5080-5100.

Supplementary European Search Report With Annex, re related application EP 07783004; Mar. 26, 2009; 5 pages.

Communication in related application EP 07783004; Nov. 2, 2010, 4 pages.

* cited by examiner

MEASUREMENT OF LINEAR AND CIRCULAR DIATTENUATION IN OPTICAL ELEMENTS

TECHNICAL FIELD

This application relates to precise measurement of linear and circular diattenuation in optical elements.

BACKGROUND AND SUMMARY

Many optical elements display a property known as diattenuation, whereby the intensity transmittance of a beam that exits an optical element or sample is a function of the polarization state of the incident beam. The intensity transmittance is a maximum $T_{max}$ for one polarization state of the incident beam, and a minimum $T_{min}$ for the orthogonal polarization state for that beam.

Linear diattenuation needs two parameters to describe it: (1) angle $\theta$ which is the angle of the maximum transmission axis for linearly polarized light; and (2) magnitude $L_d$, which is defined as $(T_{max}-T_{min})/(T_{max}+T_{min})$.

What follows is a description of a system for measuring, in addition to linear birefringence of an optical element, the linear and circular diattenuation properties of that element.

DESCRIPTION OF PREFERRED EMBODIMENTS

Figure 1:
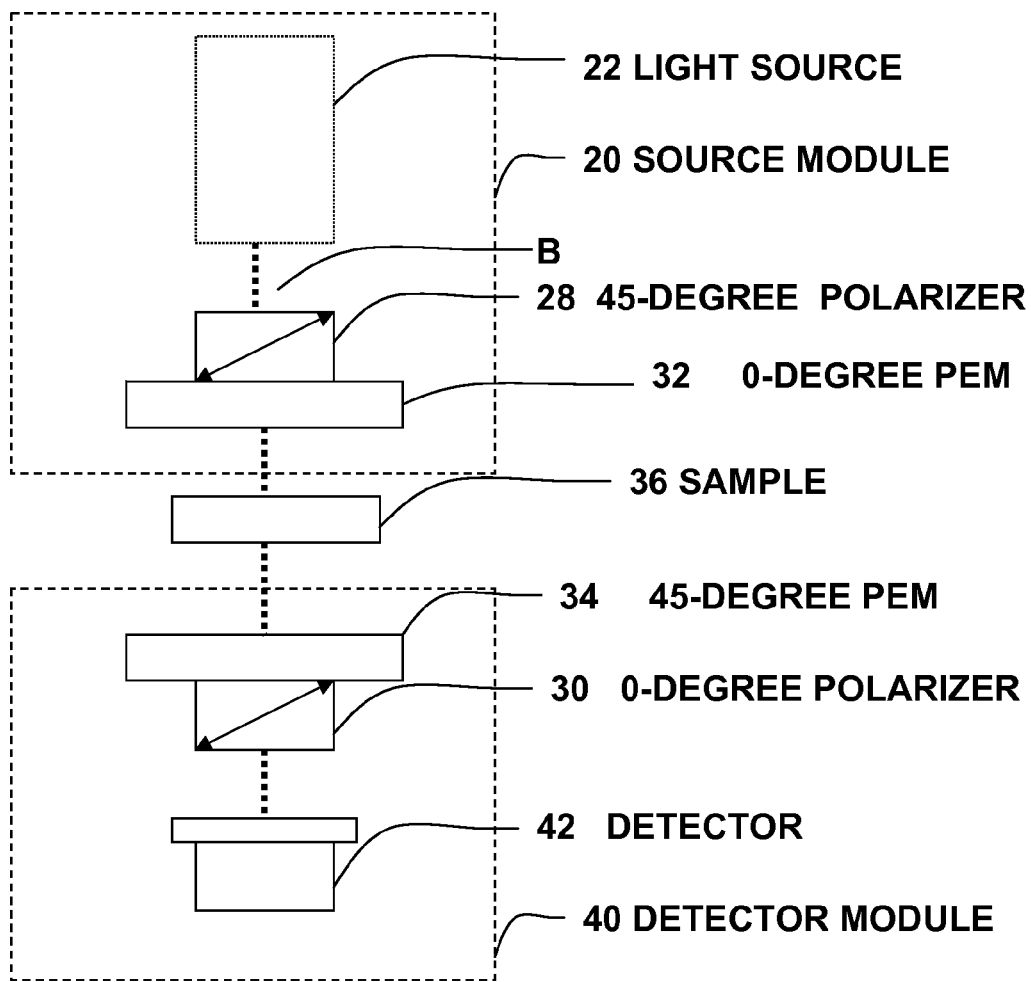
FIG. 1 is a diagram of one embodiment of the instrumentation used with the present invention, including a light source module, an optical element or sample, and a detector module.

One preferred embodiment of the present invention includes (see FIGS. 1 and 2) a light source module 20 that contains a deuterium lamp 22 (30 W), a wavelength selecting device 24 (narrow band filter) and light collimating lenses 26.

Polarizers, such as Rochon polarizers are located in the source module 20 and detector module 40 as shown. The source module polarizer 28 is oriented at 45 degrees, and the detector module polarizer 30 is oriented at 0 degrees.

A photoelastic modulator (PEM) 32 is located in the source module with its optic axis at 0 degrees. The PEM 32 modulates the polarization of the source light beam "B." A second PEM 34 is in the path of the beam "B" and is oriented at 45 degrees. The optical element of interest (hereafter sample 36) is located between the source and detector modules, hence between the two PEMs 32, 34. The two PEMs have different frequencies (for example, 50 KHz and 60 KHz, respectively).

The detector 42 may be a photomultiplier tube (PMT).

Figure 2:
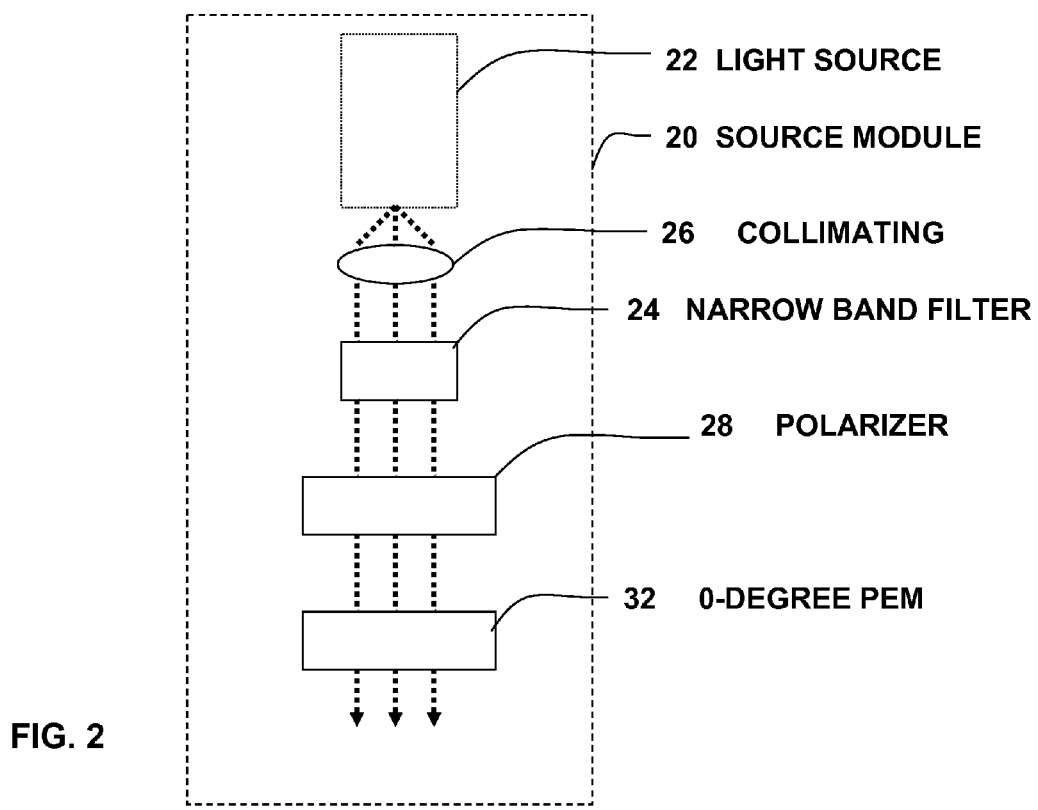
FIG. 2 is a block diagram of a preferred version of a light source module.

The instrument illustrated in FIG. 1 is essentially a polarimeter specifically designed for determining linear retardation (both magnitude and angle of fast axis) linear diattenuation (both magnitude and angle of maximum transmission axis) circular retardation and circular diattenuation in a sample. To measure both the birefringence and diattenuation of a sample, only one optical configuration, as shown in FIG. 1, is required. There is no need to rotate the source and detector modules or associated optical components.

The results of theoretical analysis using Mueller matrices for the dual PEM-single detector configuration shown in FIG. 1 are provided next.

The variables $\delta 1$ and $\delta 2$ are the time varying phase retardation of the respective PEMs 32, 34 ($\delta 1 = \delta 1_o \sin \omega_1 t$ and $\delta 2 = \delta 2_o \sin \omega_2 t$); and $\omega_1$ and $\omega_2$ are the PEM modulating frequencies of the respective PEMs 32, 34; and $\delta 1_o$ and $\delta 2_o$ being the peak retardation amplitudes of the respective PEMs 32, 34.

If the sample exhibits both linear retardation and linear diattenuation, the corresponding DC signal at the detector 42, while $\delta 1_0 = \delta 2_0 = 2.405$ radians (0.3828 waves), is:

$$V_{DC} = \frac{KI_0}{2}. \qquad \text{Eqn. (1)}$$

The useful AC terms for determining linear retardation (both magnitude and angle) and linear diattenuation (both magnitude and angle) in a sample can be obtained using the Bessel function expansions:

$$\sin\delta 1 = \sin(\delta 1_0 \sin(\omega_1 t)) = \sum_{2k+1} 2J_{2k+1}(\delta 1_0)\sin((2k+1)\omega_1 t) \qquad \text{Eqn. (2)}$$

$$\cos\delta 1 = \cos(\delta 1_0 \sin(\omega_1 t)) = J_0(\delta 1_0) + \sum_{2k} 2J_{2k}(\delta 1_0)\cos((2k)\omega_1 t) \qquad \text{Eqn. (3)}$$

and similar expansions of $\sin \delta 2$ and $\cos \delta 2$, where k is either "0" or a positive integer that represent the order of the Bessel function.

For measuring linear birefringence below a quarter of the wavelength of the light source, the useful terms are the $(2\omega_1+\omega_2)$ and $(\omega_1+2\omega_2)$ terms:

$$V_{2\omega_1+\omega_2} = \frac{KI_0}{2} 2J_2(\delta 1_0) \cdot 2J_1(\delta 2_0)\cos(2\rho)\sin\delta \qquad \text{Eqn. (4.1)}$$

$$V_{2\omega_2+\omega_1} = \frac{KI_0}{2} 2J_2(\delta 2_0) \cdot 2J_1(\delta 1_0)\sin(2\rho)\sin\delta \qquad \text{Eqn. (4.2)}$$

In order to eliminate the effect of light intensity variations due to light source fluctuations and the absorption, reflection and scattering from the sample and other optical components, the ratios of the AC signals to the DC signal are used. The ratios of AC signals to the DC signal for the $(2\omega_1+\omega_2)$ and $(\omega_1+2\omega_2)$ terms are represented in equations (5.1) and (5.2):

$$\frac{V_{2\omega_1+\omega_2}}{V_{DC}} = 2J_2(\delta 1_0) \cdot 2J_1(\delta 2_0)\cos(2\rho)\sin\delta \qquad \text{Eqn. (5.1)}$$

$$\frac{V_{2\omega_2+\omega_1}}{V_{DC}} = 2J_2(\delta 2_0) \cdot 2J_1(\delta 1_0)\sin(2\rho)\sin\delta \qquad \text{Eqn. (5.2)}$$

Defining $R_1$ and $R_2$ as corrected ratios, equations (5.1) and (5.2) become:

$$\frac{V_{2\omega_1+\omega_2}}{V_{DC}} = \frac{1}{2J_2(\delta 1_0) \cdot 2J_1(\delta 2_0)} = R_1 = \cos(2\rho)\sin\delta \quad \text{Eqn. (6.1)}$$

$$\frac{V_{2\omega_2+\omega_1}}{V_{DC}} = \frac{1}{2J_2(\delta 2_0) \cdot 2J_1(\delta 1_0)} = R_2 = \sin(2\rho)\sin\delta \quad \text{Eqn. (6.2)}$$

Rearranging equations (6.1) and (6.2), we can express the retardation magnitude and angle of fast axis of the sample as:

$$\rho = \frac{1}{2}\tan^{-1}\left[\frac{R_2}{R_1}\right] \quad \text{Eqn. (7.1) \& (7.2)}$$

or $$\rho = \frac{1}{2}ctg^{-1}\left[\frac{R_1}{R_2}\right]$$

$$\delta = \arcsin\sqrt{(R_1)^2 + (R_2)^2}$$

where $\delta$, represented in radians, is a scalar. When measured at a specific wavelength (i.e. 193 nm), it can be converted to retardation in "nm" ($\delta_{nm} = \delta_{rad} \cdot 193/(2\pi)$).

For measuring linear diattenuation, the useful terms are the $2\omega 1$ and $2\omega 2$ terms:

$$V_{2\omega_1} = \frac{KI_0}{2} 2J_2(\delta 1_0) \cdot Ld \cdot \sin(2\theta) \quad \text{Eqn. (8.1)}$$

$$V_{2\omega_2} = \frac{KI_0}{2} 2J_2(\delta 2_0) \cdot Ld \cdot \cos(2\theta) \quad \text{Eqn. (8.2)}$$

where $\theta$ is the angle of the maximum transmission axis for linearly polarized light, Ld is defined as $(T_{max} - T_{min})/(T_{max} + T_{min})$, where $T_{max}$ and $T_{min}$ are the maximum and minimum intensities of transmission for linearly polarized light.

The ratios of the AC signals to the DC signal are:

$$\frac{V_{2\omega_1}}{V_{DC}} = 2J_2(\delta 1_0) \cdot Ld \cdot \sin(2\theta) \quad \text{Eqn. (9.1)}$$

$$\frac{V_{2\omega_2}}{V_{DC}} = 2J_2(\delta 2_0) \cdot Ld \cdot \cos(2\theta) \quad \text{Eqn. (9.2)}$$

Defining $LR_1$ and $LR_2$ as corrected ratios for linear diattenuation, we have:

$$\frac{V_{2\omega_1}}{V_{DC} \cdot 2J_2(\delta 1_0)} = LR_1 = Ld \cdot \sin(2\theta) \quad \text{Eqn. (10.1)}$$

$$\frac{V_{2\omega_2}}{V_{DC} \cdot 2J_2(\delta 2_0)} = LR_2 = Ld \cdot \cos(2\theta) \quad \text{Eqn. (10.2)}$$

Rearranging equations (10.1) and (10.2), we can express the retardation magnitude and angle of fast axis of the sample as:

$$\theta = \frac{1}{2}\tan^{-1}\left[\frac{LR_1}{LR_2}\right] \quad \text{Eqn. (11.1)}$$

$$Ld = \sqrt{(LR_1)^2 + (LR_2)^2} \quad \text{Eqn. (11.2)}$$

For measuring circular diattenuation, the useful terms are the $\omega_1$ and $\omega_2$ terms:

$$V_{\omega_1} = \frac{KI_0}{2} 2J_1(\delta 1_0) \cdot Cd \quad \text{Eqn. (12.1)}$$

$$V_{\omega_2} = \frac{KI_0}{2} 2J_1(\delta 2_0) \cdot Cd \quad \text{Eqn. (12.2)}$$

where the circular diattenuation (Cd) is defined as $(T_{RCP} - T_{LCP})/(T_{RCP} + T_{LCP})$, where $T_{RCP}$ and $T_{LCP}$ are the intensities of transmission for right and left circularly polarized light, respectively.

The ratios of the AC signals to the DC signal are:

$$\frac{V_{\omega_1}}{V_{DC}} = 2J_1(\delta 1_0) \cdot Cd \quad \text{Eqn. (13.1)}$$

$$\frac{V_{\omega_2}}{V_{DC}} = 2J_1(\delta 2_0) \cdot Cd \quad \text{Eqn. (13.2)}$$

or $$Cd = \frac{V_{\omega_2}}{V_{DC} 2J_1(\delta 2_0)} = \frac{V_{\omega_1}}{V_{DC} 2J_1(\delta 1_0)} \quad \text{Eqn. (14.1)}$$

This instrument also provides the measurements of circular brief (optical rotation). Turning to a preferred implementation of the present invention, wavelength selection can be performed using a narrow band optical filter 24 (FIG. 2) (e.g. 193 nm) instead of a monochromator. This minimizes the size and weight of the source module 20 and optimize light delivery but possibly limit the wavelength resolution. Alternatively, one may use a simplified monochromator (grating at a fixed position) for selecting 193 nm light only.

Figure 3:
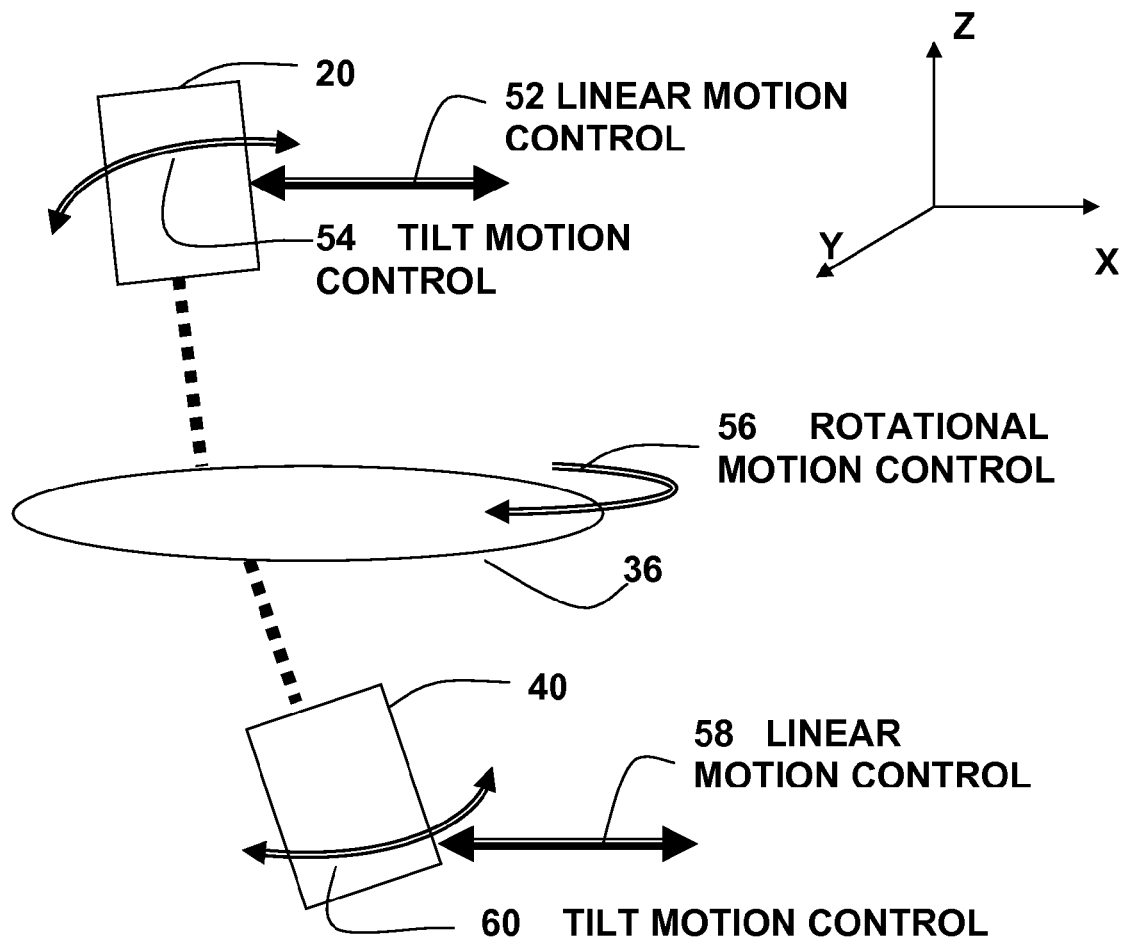
FIG. 3 is a diagram for illustrating motion controllers used with the instrument.

The system of the present invention also includes semi-automated system with software MACROs to reduce motion complexity. Five motion controls are employed (FIG. 3). The source module includes a linear translation stage 52 and a tilt stage 54. The sample 36 (in this instance, a lens of varying power and thickness) includes a rotation stage 56. The detector module includes a linear translation stage 58 and a tilt stage 60. Accordingly, the system includes five motion controllers.

The operation of the system (reference FIG. 3) includes the steps of manually generate measurement coordinates of the five motion controls for the first sample 36;

manually align source module 20 to the sample (eg, a lens) by adjusting linear motion control 52 and tilting motion control 54;

manually align detector module 40 to receive optimized light intensity by adjusting linear motion control 58 and tilting motion control 60;

Due to the symmetry of the lens sample, once the coordinates of linear motion control 52, tilting control 54, linear motion control 58 and tilting control 60 are chosen, all coordinates of the remaining (sample) rotational control 56 can be generated by rotating the lens sample one full turn; (Alternatively, the sample could be held stationary and the modules 20, 40 rotated instead.)

Create software instructions (MACRO) based on the manually generated coordinates Use MACRO for automation in subsequent measurements of the same type of lenses.

Figure 4:
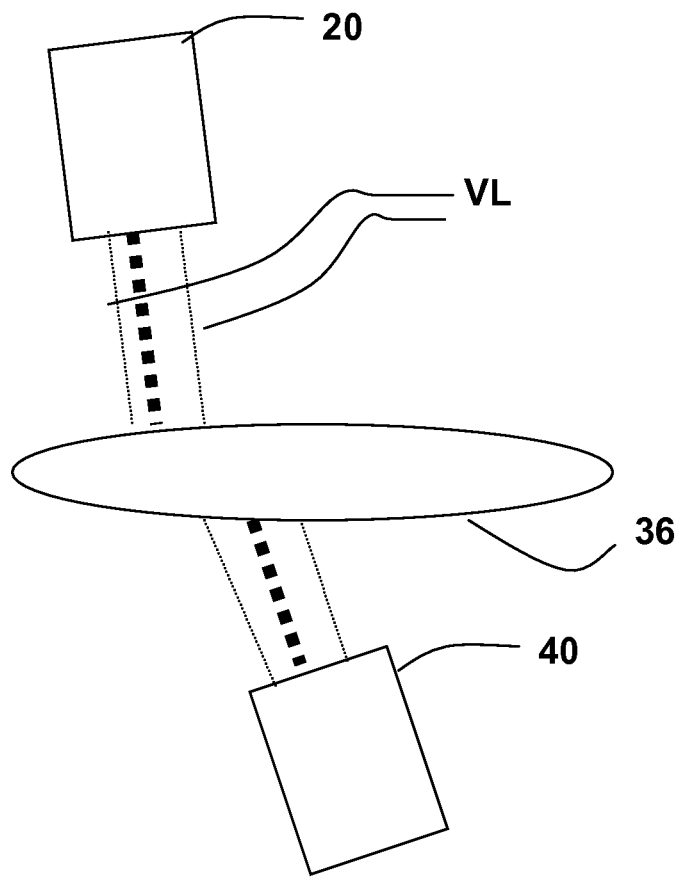
FIG. 4 is a diagram showing the use of visible laser light as a guide for the actual beam used in the measurement calculations.

The aligning steps noted above can be assisted by using two or more visible lasers as guides as shown at "VL" in FIG. 4. The lines inside of the visible laser light "VL" enclose the source light beam, which may have a wavelength of 193 nanometers, and is difficult to observe with the naked eye.

Finer motion control, if needed, can be included on one of the modules to get optimal light intensity delivery.

The advantages of using PEMs for lens measurement system include a large useful aperture and acceptance angle.

Figure 5:
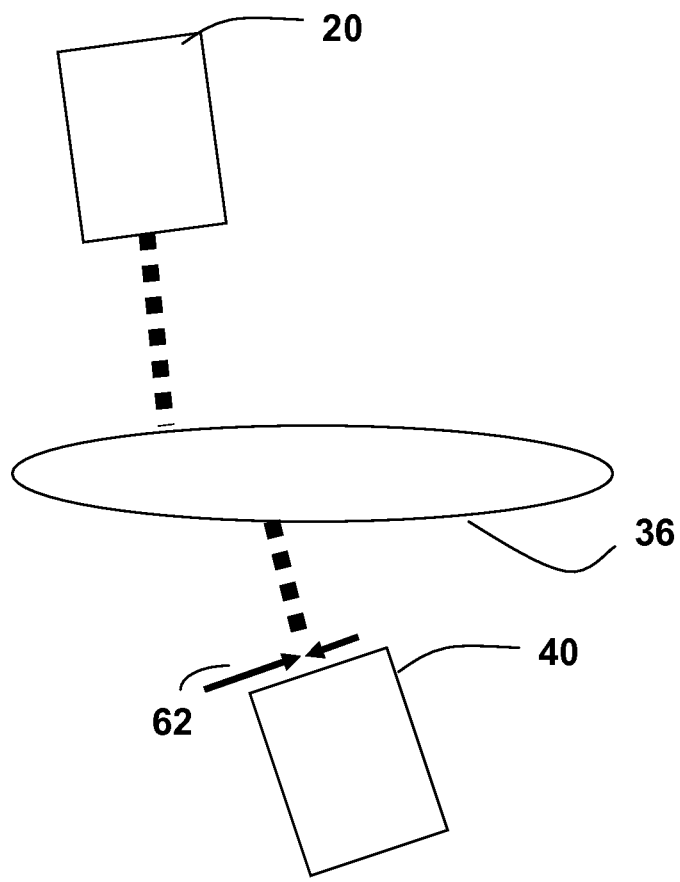
FIG. 5 is diagram illustrating a variable aperture for use in a detector module in instances where the source light beam collimation is modified by the sample.

As respects the treatment of a non-collimated beam exiting the (lens) sample 36 one could use aperture diameter control 62 (represented by the opposed arrows in FIG. 5), which, like the motion controllers discussed above, may be computer controlled. The diameter of the aperture is related to the amount of convergence or divergence of the light beam introduced by the sample 36, which, as noted can be a lens of varying optical power.

Figure 6:
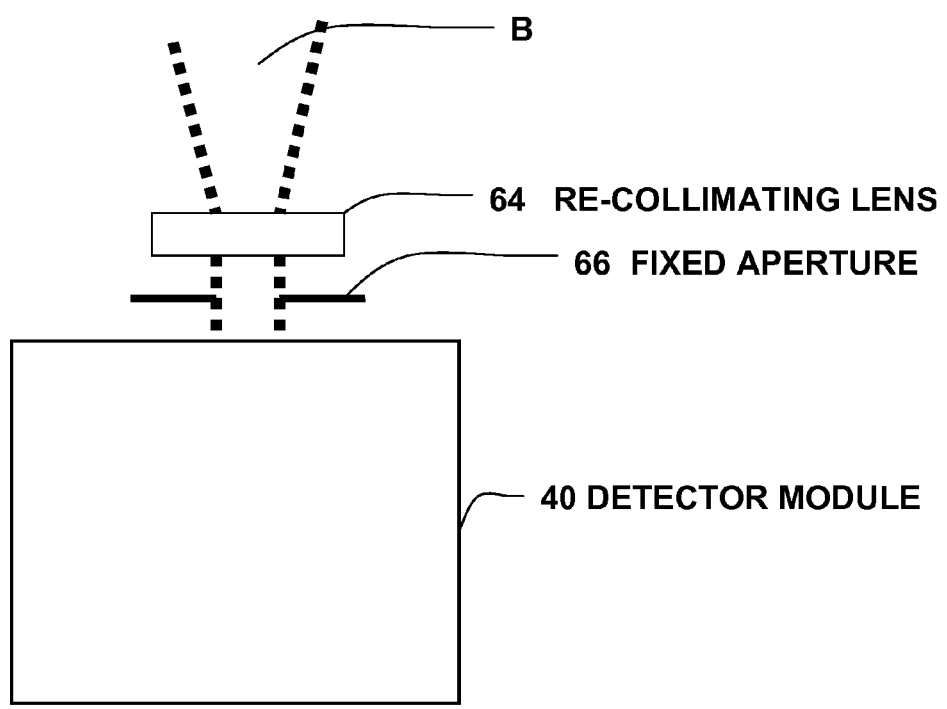
FIG. 6 is a diagram showing the use of a re-collimating lens and fixed aperture for use in a detector module in instances where the light beam collimation is modified by the sample.

Alternatively, one could use a re-collimating lens 64 and a fixed aperture 66 in front of active area of the detector (see FIG. 6). The focused or diverged beam B emanating from the sample lens under measurement is directed to that re-collimating lens 64 before passing through the fixed aperture 66.

While the present invention has been described in terms of preferred embodiments, it will be appreciated by one of ordinary skill in the art that modifications may be made without departing from the teachings and spirit of the foregoing.

The invention claimed is:

1. A system for measuring diattenuation in an optical element comprising:
 a sample rotation stage for securing an optical element sample;
 a light source module for generating a source light beam;
 a detector module; the light source module and detector module being arranged with the sample rotation stage between them, thereby permitting the source light beam to propagate through a sample that may be secured in the sample stage and to the detector module;
 linear motion means for controlled linear motion of the light source module and for controlling linear motion of the detector module;
 first tilt means for controlled tilt of the light source module and source beam,
 rotation means for rotating the sample rotation stage and
 second tilt means for tilting the detector module, thereby to facilitate detection, by the detector module, of light intensity information corresponding to diattenuation characteristics of the optical sample secured in the sample stage.

2. The system of claim 1 wherein the light source module and the detector module each include a photoelastic modulator for modulating the polarization of the beam.

3. The system of claim 1 wherein the light source module is configured to generate in addition to the source light beam an alignment beam of visible light thereby to facilitate alignment of the light source module and the detector module.

4. The system of claim 3 wherein the light source beam has a wavelength of about 193 nanometers.

5. The system of claim 1 including a sample having a varying thickness and power that causes the source light beam to converge, and wherein the detector module includes an active area for receiving light; and
 aperture means associated with the detector module for effectively changing the active area of the detector module by an amount related to the amount of convergence caused by the sample.

6. The system of claim 1 including a sample having a varying thickness and power that causes the source light beam to diverge, and wherein the detector module includes an active area for receiving light; and
 aperture means associated with the detector module for effectively changing the active area of the detector module by an amount related to the amount of divergence caused by the sample.

7. The system of claim 1 including a sample having a varying thickness and power; and wherein the detector module includes an active area for receiving light; and
 aperture means associated with the detector module for effectively changing the active area of the detector module.

8. The system of claim 1 including a sample having a varying thickness and power; and wherein the detector module includes an active area for receiving light; and
 a collimating lens disposed between the sample and the active area of the detector module.

9. The system of claim 1 wherein the light source beam is polarized and modulated using a photoelastic modulator, and the modulated light intensity information corresponds to the linear and circular diattenuation characteristics of the optical sample.

10. A method of measuring diattenuation in an optical element comprising the steps of:
 securing an optical element sample in a rotatable stage;
 generating a polarized and modulated source light beam;
 directing the source beam through the sample by
  using linear motion means for controlled linear motion of the light source module; and
  using first tilt means for controlled tilt of the light source module;
 arranging the active area of a detector to detect the source light beam after it propagates through the sample by
  using linear motion means for controlled linear motion of the detector module; and
  using second tilt means for tilting the detector module; and
 determining, from the detected source light, information corresponding to a diattenuation characteristic of the optical sample secured in the sample stage.

11. The method of claim 10 including the step of modulating the polarization of the source light beam using photoelastic modulators before and after the light beam propagates through the sample.

12. The method of claim 10 wherein the arranging step includes the step of generating in addition to the source light beam an alignment beam of visible light thereby to facilitate alignment of the source light beam and the detector.

13. The method of claim 12 including the step of selecting the source light beam to have a wavelength of about 193 nanometers.

14. The method of claim 10 wherein the arranging step includes the step of effectively changing the active area of the detector by an amount corresponding to the degree with which the sample converges or diverges the source light beam.

15. The method of claim 10 wherein the arranging step includes the step of collimating the source light beam after that beam propagates through the sample.

16. The method of claim 10 wherein the determining step includes determining the circular diattenuation of the optical sample.

* * * * *